United States Patent [19]
Wirth et al.

[11] 3,936,422

[45] Feb. 3, 1976

[54] ANTI-STATIC MODIFIED THERMOPLASTICS

[75] Inventors: Hermann O. Wirth, Bensheim-Averbach; Hans-Helmut Friedrich, Lindenfels, Odenwald, both of Germany; Helmut Linhart, Reinach, Switzerland

[73] Assignee: Ciba-Geigy Corporation, Ardsley, N.Y.

[22] Filed: Jan. 7, 1975

[21] Appl. No.: 539,139

[30] Foreign Application Priority Data
Jan. 10, 1974 Switzerland.......................... 286/74

[52] U.S. Cl................. 260/45.95 N; 260/2.5 AG; 260/2.5 BB; 260/2.5 A; 260/30.8 R; 260/77.5 A; 260/78 S; 260/94.7 S; 260/92.8 A; 260/DIG. 15
[51] Int. Cl.$^2$............................................ C08K 5/36
[58] Field of Search...... 260/2.5 AG, 2.5 BB, 2.5 A, 260/45.95 N, 94.7 S, 92.8 A, DIG. 15, 30.8, 78 S, 77.5 A

[56] References Cited
UNITED STATES PATENTS

| | | | |
|---|---|---|---|
| 2,468,309 | 4/1949 | Sibley | 260/45.95 N |
| 2,564,795 | 8/1951 | Sibley | 260/45.95 N |
| 2,570,050 | 10/1951 | Eky | 260/45.95 N |
| 2,874,192 | 2/1959 | Cottle et al. | 260/45.95 N |
| 2,995,539 | 8/1961 | Barker et al. | 260/45.95 N |
| 3,705,139 | 12/1972 | Yamane et al. | 260/92.8 A |
| 3,743,679 | 7/1973 | Hickner et al. | 260/45.95 N |
| 3,879,346 | 4/1975 | Friedrich et al. | 260/DIG. 45 |

Primary Examiner—V. P. Hoke
Attorney, Agent, or Firm—Luther A. R. Hall

[57] ABSTRACT

Reaction products of mercaptans, ethylene oxide and/or propylene oxide with glycidol are effective antistatic agents when added to thermoplastics, and often also act as processing stabilisers.

16 Claims, No Drawings

ANTI-STATIC MODIFIED THERMOPLASTICS

The present invention relates to thermoplastics containing, as substances which have an anti-static action and which improve processability, reaction products of mercaptans with ethylene oxide and/or propylene oxide and with glycol, to the reaction products and to a process for their manufacture.

In German Offenlegungsschrift 2,021,083, p-alkylphenoxypoly(hydroxyalkylene oxides) are described as surfaceactive compounds which, when used in stabiliser baths, serve to improve colour photographic developing processes. The problem of imparting an anti-static finish to thermoplastics is, however, not mentioned in this Offenlegungsschrift.

DT-OS 1,930,343 discloses photographic films which, for example, consist of a thermoplastic and a further layer applied thereto and which contain, in order to prevent electrostatic charge, a reaction product from glycidol and at least one epoxidised, linear, aliphatic alcohol. It has been found, however, that the anti-static effect of these substances after incorporation into a plastic is insufficient for practical purposes. The polyalkyleneglycol ethers described in DT-AS 1,292,408 also yield, in practice, only unsatisfactory results owing to their relatively low anti-static action.

For a broad field of application of substances which have an anti-static action it is desirable that these substances have a liquid consistency in order to facilitate their incorporation and dispersion in the plastic. It is the task of the present invention to provide substances, with an anti-static effect, which have improved properties in respect of processing technology, but without their antistatic and stabilising properties being thereby substantially reduced.

The present invention relates to anti-static plastics, having good processing stability, which contain 0.01 to 5, preferably 0.05 to 2, % by weight, relative to the plastic, of a substance of the formula I, or mixtures thereof,

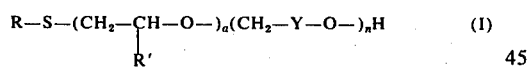
$$R-S-(CH_2-CH-O-)_a(CH_2-Y-O-)_nH \quad (I)$$
$$R'$$

wherein R' denotes a hydrogen atom and/or the methyl group, Y denotes

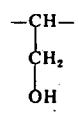
$$-CH-$$
$$CH_2$$
$$OH$$

and or

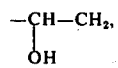
$$-CH-CH_2,$$
$$OH$$

a denotes, as an average value, a number between 1.0 and 12, n denotes, as an average value, a number from 0.5 to 8, preferably 1 to 4, and R denotes a linear or branched alkyl radical having 8 to 24 carbon atoms, which can preferably be interrupted once by the groups $-CO_2-$, $-O-$ or $-S-$, or denotes phenyl, phenyl substituted by linear or branched alkyl groups which preferably contain 1 to 15 carbon atoms, or phenylalkylene having 1 to 3, preferably 1, carbon atoms in the alkylene chain, it being possible for the alkylene chain or the linkages thereof to the phenyl group to be interrupted by a $-CO_2-$ group or an oxygen or sulphur atom, and for the phenyl radical thereof also to be substituted by linear or branched alkyl groups, and in all cases the whole radical contains 7 to 30, preferably 10 to 20, carbon atoms, it being possible, for the case where R' is the methyl group, for R also to denote a linear or branched alkyl radical having 1 to 7 carbon atoms, and in all cases of R the sum of the carbon atoms of R and of the radical

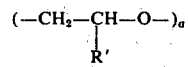
$$(-CH_2-CH-O-)_a$$
$$R'$$

in formula I being 8 to 40, preferably 10 to 25 and particularly 10 to 20, and optionally contain further additives.

R preferably denotes an alkyl radical, a, as an average value, is preferably a number between 1 and 6, and R' represents a hydrogen atom, R preferably denotes an alkyl radical having 12 to 18 carbon atoms and R' represents a hydrogen atom, and R' preferably represents a hydrogen atom or the methyl group.

In formula I, R particularly preferentially denotes an alkyl radical having 12 to 18 carbon atoms or a phenyl or benzyl radical which is substituted by alkyl groups and which has a total of 10 to 20 carbon atoms, R' denotes a hydrogen atom, a denotes, as an average value, a number between 1 and 6, and n denotes, as an average value, a number from 1 to 4, or, in formula I, R denotes an alkyl radical having 6 to 22 carbon atoms or a phenyl or benzyl radical which is substituted by alkyl groups and which has 10 to 20 carbon atoms, R' denotes the methyl group, n denotes, as an average value, a number from 1 to 4, and the sum of the carbon atoms in the radical R and in the radical

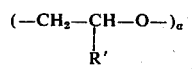
$$(-CH_2-CH-O-)_a$$
$$R'$$

is 10 to 25, particularly 10 to 20. In the case where R' is the methyl group, it is particularly preferred that, if R represents a radical having up to 10 carbon atoms, a represents, as an average value, a number of at least 3, and, if R represents a radical having more than 16 carbon atoms, a denotes, as an average value, a number of not more than 3.

The invention further relates to the substances of the formula I and to a process for their manufacture. Examples of suitable thermoplastics which can be used are: preferably polyolefines, particularly polypropylene and high-pressure polyethylene, and also polyvinyl chloride and polyurethane.

Examples of R in formula I are:
 a. methyl, butyl, octyl, lauryl; t-dodecyl, hexadecyl, octadecyl and tetracosyl;
 b. n-alkyls, as radicals of corresponding mercaptans which, in analogy to the synthesis reactions described by ZIEGLER for the production of alcohols, are accessible starting from aluminium, hydrogen and ethylene, with subsequent "sulphurisation." The substances here need not be molecularly homogeneous.

| | |
|---|---|
| Butyl—O—CO—CH₂—CH₂— | lauryl—O—(CH₂—CH₂—O)₇— CO—CH₂— |
| i—octyl—O—CO—CH₂— | n—heptyl—CO—O—CH₂—CH₂— |
| n—dodecyl—O—CO—CH₂—CH₂— | lauryl—S—CH₂—CH₂— |
| n—octadecyl—O—CO—CH₂— | octyl—S—CH₂—CH₂— |
| i—octadecyl—O—CO—CH₂—CH₂— | i—octyl—O—CH₂—CH₂— |
| butyl—O—CH₂—CH₂—O—CO—CH₂— | | and also phenyl, methylphenyl, butylphenyl, dibutylphenyl, octylphenyl, dodecylphenyl, hexadecylphenyl, tetracosylphenyl, didodecylphenyl, benzyl, phenylethyl, phenylpropyl, ethylbenzyl, butylbenzyl, dodecylbenzyl, octylphenylethyl, methylbutylbenzyl, phenyl—CO—O—CH₂—CH₂, dodecylphenyl-O—CH₂—CH₂ or butylphenyl—CH₂—O—CH₂—CH₂—.

Preferred examples of R are: ethyl, butyl, hexyl, octyl, hexadecyl, octadecyl, t-dodecyl, benzyl, dodecylbenzyl, i—octyl—O—CO—CO₂—, phenyl—CO—O—CH₂—CH₂—, n-butyl—O—CH₂—CH₂— or n-octyl-S—CH₂—CH₂—.

The substances according to the invention are new and are prepared by processes which are in themselves known. For this purpose, mercaptans of the formula II are used as starting materials and are reacted, in the presence of anionic or cationic catalysts and optionally a solvent, with ethylene oxide and/or propylene oxide (formula III):

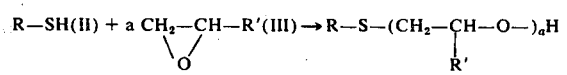

The intermediate products thus formed are then reacted, in the presence of a catalyst and optionally in the presence of a solvent, with glycidol to give the substances of the formula I:

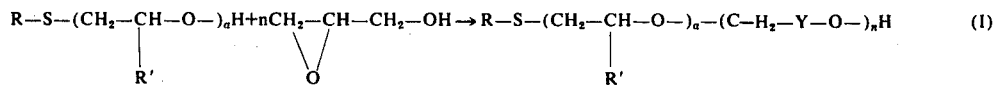

In the above equation, R, R', Y, a and n have the same meaning as in formula I.

Suitable catalysts for the epoxide addition reactions are anionic systems, such as sodium amide, sodium alcoholate, sodium hydride, or potassium t-butylate. If conditions are observed, it is also possible to use alkali metal hydroxides. The reaction temperature must be above 100°C, advantageously above 130°C, since, below 100°C, only a single epoxide group is added on.

In principle, the epoxidation can also be carried out cationically. Suitable catalysts are, above all, ansolvoacids, but preferably tin tetrachloride. In this case the epoxidation must also be carried out above 100°C, advantageously at about 120°C. In the case of higher degrees of epoxidation, a repeated addition of catalyst can be necessary.

Ethylene oxide and propylene oxide can also be employed conjointly. This can be carried out in such a way that both epoxy compounds are added as a mixture. However, it is advantageous to proceed by first employing the propylene oxide and then the ethylene oxide. The glycidolisation is then carried out subsequently.

The addition reaction with glycidol can also be carried out under anionic conditions; in this case, the same conditions must be maintained as in the case of the epoxidation reaction. The intermediate product obtained in the epoxidation can, in this case, be isolated beforehand or it can be directly reacted further. If the glycidolisation is carried out directly following the addition of ethylene oxide or of propylene oxide, a further addition of catalyst is also generally unnecessary, at least not in the case of low degrees of epoxidation.

In principle, the glycidolisation can also be carried out cationically. Cationic catalysis is advisable particularly when the reaction is carried out in two stages, if the intermediate stages which are obtained after the epoxidation are isolated or are directly employed as such (for example in the form of commercial products). In this case the further addition of a catalyst is necessary.

The use of a solvent is generally not necessary. Suitable solvents for the cationic catalysis are halogenated aromatic substances, such as chlorobenzene or dichlorobenzene. High-boiling ethers, above all, such as dibutyl ether or anisole, have proved suitable for the anionic catalysis of the epoxide addition reaction.

The products formed under the conditions described, (with anionic or cationic catalysis) generally contain the epoxide units propylene oxide and/or ethylene oxide and glycidol in a statistical distribution. a and n in formula I therefore represent statistical average values. Very probably there is a POISSON distribution.

In the glycidolisation reaction, two types of structure can be formed

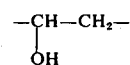

or

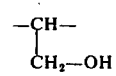

which are equally designated by Y in formula I. One or the other or a mixture of both types can be preferentially formed, depending on the reaction conditions.

The substances of the formula I are incorporated into the plastics in an amount of 0.01 to 5, preferably 0.05 to 2, particularly preferentially 0.1 to 1.0% by weight.

The incorporation can be carried out after polymerisation, for example by mixing the substances and optionally further additives into the melt by the methods which are customary in the art, before or during moulding. The substances can also be incorporated into the polymers which are to be given an anti-static finish, in the form of a master-batch containing these compounds, for example, in a concentration of 2.5 to 25% by weight. Further details of the incorporation can be obtained from the main patent.

In principle, the substances of formula I can also be used for external anti-static finishing. In these cases, the application can be carried out in a dissolved state by dipping or spraying. Examples of suitable solvents are ethanol, acetone, ethyl acetate and i-propanol, and also mixtures with water. Aqueous emulsions are also suitable systems. However, these methods do not give such good results and incorporation in the plastic is, therefore, the particularly preferred embodiment.

The customary additives of all kinds for the processing and use of these polymers, such as, for example, plasticisers, heat-stabilisers, antioxidants, dyestuffs, fillers, reinforcing fillers, lubricants, pigments and/or flameproofing agents can be added to the thermoplasts conjointly with the substances of the formula I which are to be used in accordance with the invention.

Anti-static shaped articles of all kinds can be produced from the plastic moulding compositions according to the invention by the customary moulding processes, such as injection moulding, calendering or extrusion.

An anti-static effect of substances which are structurally very similar, but which only contain oxygen, has already been described (compare DT-OS 1,930,343). This property has also been established in the case of substances which are characterised in formula I by the replacement of sulphur by oxygen and in the case where R' is the methyl group and R is an alkyl radical. However, the sulphur-containing substances of the formula I have, surprisingly, a substantially better anti-static effect, particularly if they are incorporated into the thermoplastic. This improvement could not be foreseen, above all in that it is achieved by the mere replacement of an oxygen atom by a sulphur atom.

A substantial advantage is to be seen in the additional effect of stabilising processing, that is to say prevention of discolouration of the substrate, which is particularly relevant in the case of polyolefines, which undergo during processing a thermal-oxidative degradation or discolourations based on other reactions, a degradation which cannot generally be completely eliminated even by means of antioxidants, such as hindered phenols or other stabilisers. Another advantage is the increased intrinsic stability and lower volatility of the substances of the formula I, which makes high processing temperatures possible for corresponding thermoplasts, and so makes possible an increase in output in the processing step. Furthermore, these substances are distinguished by being physiologically acceptable and by their low reactivity towards other additives, for example phenolic antioxidants. In general, they are mobile to oily substances, from which fact the desired advantage of improved ability to be incorporated and improved dispersion in the polymer is evident.

The examples which follow illustrate the invention in greater detail. In these, percentages denote % by weight and parts denote parts by weight. The substances are characterised analytically by determination of the total OH content by acetylation, and by means of the average molecular weight, which is determined by means of vapour pressure osmometry. Table 1 gives the chemical composition and physical properties. The technological tests and testing methods are quoted in the particular examples.

A. SYNTHESIS OF THE ACTIVE SUBSTANCES

EXAMPLE 1

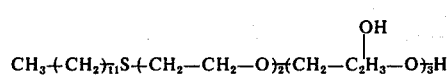

101 g of 1-dodecanethiol and 0.5 g of sodium hydride are heated to 145°C and 44 g of ethylene oxide are added by means of a cooled filter funnel at the same temperature; the mixture is subsequently stirred until the ethylene oxide is reacted (no reflux). 111 g of glycidol are then added dropwise at the same temperature. After the dropwise addition the mixture is stirred for a further 30 minutes at 150°C. Yield: practically 100% of theory; yellow liquid of low viscosity OH calculated 13.27%, found 12.8% molecular weight calculated 512, found 486

EXAMPLE 2

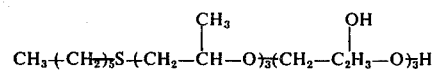

59 g of 1-hexanethiol and 0.5 g of sodium amide are initially taken. The ammonia thus formed is removed by applying a vacuum. The mixture is then heated to 145°C and 87 g of propylene oxide are added in such a way that a temperature of 140° - 150°C is maintained. Stirring is continued until the propylene oxide is reacted (no reflux). 111 g of glycidol are then added dropwise at the same temperature. After the completion of the dropwise addition, the mixture is stirred for a further 30 minutes at 150°C.

Yield: practically 100% of theory; yellowish liquid OH calculated 13.22%, found 13.0% molecular weight calculated 515, found 475

EXAMPLE 3

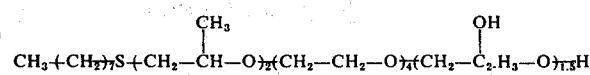

73 g of 1-octanethiol and 0.7 g of sodium hydride are heated to 145°C and are reacted at the same temperature with 58 g of propylene oxide and subsequently with 88 g of ethylene oxide. 111 g of glycidol are then added dropwise in such a manner that the temperature always remains at 140° - 150°C. After the completion of the addition, the mixture is stirred for 30 minutes at 150°C.

Yield: practically 100% of theory; yellowish liquid OH calculated 9.45%, found 9.1% molecular weight calculated 450, found 435

EXAMPLE 4

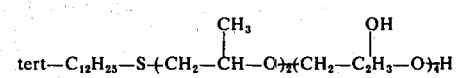

50.6 g of tert.-dodecylmercaptan and 0.5 g of sodium hydride are reacted at 140° - 150°C with 29 g of propylene oxide. The reaction mixture is then treated with 1/10 N sulphuric acid/diethyl ether in order to remove the catalyst. After distilling off the ether and drying in vacuo, 0.8 g of tin(IV) chloride is added to the reaction product and 74 g of glycidol are added dropwise at 120°C. After the completion of the addition, the mixture is stirred for a further 30 minutes at the same temperature.

Yield: practically 100% of theory; yellowish liquid of low viscosity OH calculated 13.83%, found 13.4% molecular weight calculated 615, found 580

EXAMPLE 5

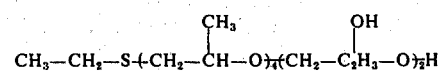

31 g of ethanethiol, 1 g of sodium methylate and 116 g of propylene oxide are heated to 140° – 150°C for 2 hours in an autoclave. After cooling to room temperature, the reaction product is worked up using 1/10 N sulphuric acid/diethyl ether and is purified by means of active charcoal.

After drying the reaction product in an oil pump vacuum, 1.1 g of tin(IV) chloride are added and the mixture is then treated at 120°C with 74 g of glycidol. After the addition is completed, the reaction mixture is stirred for a further 30 minutes at 130°C.

Yield: practically 100% of theory; yellow liquid OH calculated 11.53%, found 11.0% molecular weight calculated 443, found 418

The conditions of synthesis and the properties of further active substances can be seen in Table 1 (Examples 6 – 47).

Table 1

(Examples 6 to 47)
Physico-chemical criteria for active substances corresponding to the present invention.
(The calculated analytical figures are in brackets)

| Example No. | Starting product | Conditions of synthesis (according to Example) | Degree of epoxidation Propylene oxide (a) | Ethylene oxide (a) | Glycidol (n) | Analytical Data % total OH | Molecular weight |
|---|---|---|---|---|---|---|---|
| 6 | $CH_3-CH_2-SH$ | 5 | 4 | — | 1 | 8.8 (9.23) | 382 (369) |
| 7 | | 5 | 4 | — | 4 | 12.9 (14.39) | 540 (591) |
| 8 | | 5 | 4 | — | 6 | 15.2 (16.11) | — (739) |
| 9 | $CH_3-(CH_2)_5SH$ | 2 | 3 | — | 3 | 12.7 (13.22) | 473 (515) |
| 10 | | 2 | 5 | — | 3 | 10.3 (10.78) | — (631) |
| 11 | $CH_3-(CH_2)_3O-CH_2-CH_2-SH$ | 1 | 3 | — | 2 | 10.9 (11.17) | 411 (457) |
| 12 | | 1 | 5 | — | 2 | 8.5 (8.91) | 548 (573) |
| 13 | | 1 | 10 | — | 4 | 8.3 (8.41) | — (1011) |
| 14 | $i-C_8H_{17}-O-CO-CH_2-SH$ | 2 | 1.2 | — | 2 | 11.6 (12.09) | 383 (422) |
| 15 | | 2 | 3 | — | 3 | 11.1 (11.32) | — (601) |
| 16 | $CH_3-(CH_2)_{11}SH$ | 2 | 1.5 | — | 1 | 9.2 (9.34) | 344 (364) |
| 17 | | 2 | 1.5 | — | 2 | 11.1 (11.66) | 396 (438) |
| 18 | | 2 | 2 | — | 3 | 12.3 (12.58) | 520 (541) |
| 19 | | 2 | 5 | — | 4 | 10.5 (10.78) | — (789) |
| 20 | $tert-C_{12}H_{25}-SH$ | 4 | 2 | — | 2 | 10.5 (10.98) | 480 (467) |
| 21 | | 4 | 2 | — | 8 | 15.8 (16.80) | — (911) |
| 22 | —$CH_2-SH$ | 4 | 2 | — | 2 | 12.9 (13.13) | 371 (388) |
| 23 | | 4 | 2 | — | 5 | 16.1 (16.71) | —(611) |
| 24 | $CH_3-(CH_2)_7SH$ | 1 | — | 1.7 | 2 | 13.9 (13.81) | 352 (369) |
| 25 | | 1 | — | 1.7 | 3 | 14.8 (15.34) | 420 (443) |
| 26 | $CH_3-(CH_2)_7-S-CH_2-CH_2-SH$ | 1 | — | 2 | 1 | 9.2 (9.23) | 348 (369) |
| 27 | | 1 | — | 2 | 3 | 12.9 (13.17) | 528 (517) |
| 28 | $CH_3-(CH_2)_{11}SH$ | 1 | — | 1.5 | 1 | 9.7 (9.93) | 340 (343) |
| 29 | | 1 | — | 3.1 | 1.2 | 8.8 (8.74) | 395 (428) |
| 30 | | 1 | — | 5 | 5 | 12.5 (12.87) | — (793) |
| 31 | $tert-C_{12}H_{25}-SH$ | 1 | — | 1.5 | 3 | 13.8 (13.86) | 460 (491) |
| 32 | | 1 | — | 2.5 | 7 | 15.5 (16.37) | — (831) |
| 33 | $CH_3-(CH_2)_{17}SH$ | 1 | — | 1.5 | 1 | 7.8 (7.97) | 400 (427) |
| 34 | | 1 | — | 1.5 | 2 | 10.0 (10.19) | 507 (501) |
| 35 | | 1 | — | 3 | 0.5 | 5.8 (5.60) | 411 (456) |
| 36 | | 1 | — | 6 | 6 | 12.0 (11.96) | — (995) |
| 37 | | 1 | — | 10 | 4 | 8.2 (8.31) | — (1023) |
| 38 | —$CO-O-CH_2-CH_2-SH$ | — | | 1.3 | 2 | 12.4 (12.37) | 383 (412) |
| 39 | | 4 | — | 2 | 5 | 15.2 (15.93) | — (641) |
| 40 | $CH_3-(CH_2)_{11}$——$CH_2-SH$ | 1 | — | 3 | 1 | 6.7 (6.82) | 481 (499) |
| 41 | | 1 | — | 5 | 3 | 9.1 (9.26) | — (735) |
| 42 | $CH_3-(CH_2)_7SH$ | 3 | 2 | 4 | 1.5 | 7.8 (7.73) | 535 (549) |
| 43 | | 3 | 2 | 2 | 2 | 10.1 (10.23) | 477 (499) |
| 44 | $CH_3-(CH_2)_{11}SH$ | 3 | 2 | 2 | 2 | 8.9 (9.20) | 507 (555) |
| 45 | | 3 | 2 | 4 | 1 | 6.0 (5.98) | 551 (569) |
| 46 | —$CH_2-SH$ | 3 | 3 | 4 | 2 | 8.1 (8.19) | —(623) |
| 47 | | 3 | 5 | 2 | 3 | 9.0 (9.38) | — (725) |

B. Technological Test Data

I. Anti-static effect (Examples 48 – 93)

After being incorporated into the thermoplastics mentioned intially, the active substances described in Section A are tested for anti-static effect with the aid of an apparatus specially developed for this purpose.

The principle of measurement is very simple. A needle electrode, which is induced to a corona discharge by means of a high frequency electric field via a positively or negatively polarised primary voltage, is located on a rotor disc which moves synchronously above the test piece (dimensions 40 × 40 × 0.1 to 1 mm). This corona discharge causes an electrostatic charge on the test piece. A measuring condenser, which scans inductively the electric field building up on the test piece, is also located on the rotor disc. In the stationary state, which is achieved after a very short time, the measuring device indicates the intensity of the field produced by the corona discharge. This is a measure of the tendency to acquire a charge (expressed in mV of charge level).

After switching off the corona current, the charge on the test piece is reduced — in dependence on the surface resistance. This process can be followed as a function of time with the aid of a recorder. The time after which the field or the charge has decayed to one half is called the half-life period; it is a measure of the surface conductivity and is quoted in seconds of half-life periods.

This measurement is carried out in an air-conditioned chamber at a relative atmospheric humidity of 50% and at 22°C. The test pieces are also conditioned in this chamber for a few days before the measurement.

The preparation of the test pieces from the active substances and from the suitable thermoplastics is described in the main patent to which reference is made. The results of the measurements are summarised in Table 2. The abbreviations used for the various polymers under "Substrate (Plastic)" denote:

PP: polypropylene
ldpe: high pressure polyethylene
hdpe: low pressure polyethylene
PU: polyurethane
PAN: polyacrylonitrile
PA: polyamide
PVC (P): polyvinyl chloride (plasticised)

II. Example 48 (comparison example)

The substance described in Example 29 is compared, in respect of its anti-static effect in polypropylene, with the similar substance, which is an oxygen analogue and which has the following formula (compare DT-OS 1,930,343):

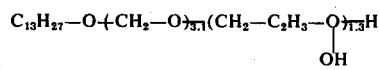

The concentration of additive was 0.5% in each case. For the substance of the above formula, the charge level is 900 mV and the half-life period is infinite.

The sulphur-containing substance in Example 29 has a substantially better anti-static effect (compare also Table 2).

III. Effect on processing stability (Examples 94 – 97)

The effect of the substances described here in stabilising the processing of various types of polyolefine is tested by means of the melt index on multiple extrusion in a screw extruder at 230°C and a throughput of 2.16 kg. The incorporation is carried out at 260°C and 100 r.p.m. The values measured can be seen in Table 3.

Table 2

(Examples 49 to 93)

Results of the anti-static testing of various thermoplastics

| Example No. | Test substance (Example No.) | Substrate (plastic) | Additive concentration (%) | Charge level (mV) | Half-life period (seconds) |
|---|---|---|---|---|---|
| 49 | — | PP | — | 1100 | ∞ |
| 50 | 9 | PP | 0.5 | 900 | 4.0 |
| 51 | 11 | PP | 0.5 | 950 | 3.2 |
| 52 | 16 | PP | 0.5 | 600 | 0.5 |
| 53 | 17 | PP | 0.5 | 550 | 0.3 |
| 54 | 20 | PP | 0.5 | 600 | 0.8 |
| 55 | 22 | PP | 0.5 | 800 | 4.2 |
| 56 | 24 | PP | 0.5 | 650 | 1.0 |
| 57 | 26 | PP | 0.5 | 600 | 0.7 |
| 58 | 28 | PP | 0.5 | 500 | 0.4 |
| 59 | 33 | PP | 0.5 | 500 | <0.3 |
| 60 | 34 | PP | 0.1 | 1000 | >10 |
| 61 | 34 | PP | 0.2 | 900 | 8 |
| 62 | 34 | PP | 0.3 | 660 | 0.5 |
| 63 | 34 | PP | 0.5 | 500 | <0.3 |
| 64 | 35 | PP | 1.0 | 700 | 0.8 |
| 65 | 40 | PP | 0.5 | 550 | <0.3 |
| 66 | 44 | PP | 1.0 | 600 | 1.2 |
| 67 | 29 | PP | 0.5 | 550 | 0.3 |
| 68 | — | ldpe | — | 1100 | ∞ |
| 69 | 16 | ldpe | 0.5 | 200 | 0.3 |
| 70 | 17 | ldpe | 0.5 | 300 | 0.3 |
| 71 | 24 | ldpe | 0.3 | 300 | 0.3 |
| 72 | 28 | ldpe | 0.3 | 280 | 0.3 |
| 73 | 29 | ldpe | 0.3 | 200 | 0.3 |
| 74 | 33 | ldpe | 0.5 | 200 | 0.3 |
| 75 | 34 | ldpe | 0.5 | 220 | 0.3 |
| 76 | — | hdpe | — | 1100 | ∞ |
| 77 | 10 | hdpe | 1.0 | 900 | 4.5 |
| 78 | 18 | hdpe | 1.0 | 320 | <0.3 |
| 79 | 25 | hdpe | 1.0 | 500 | 2.5 |
| 80 | 31 | hdpe | 1.0 | 480 | 3.2 |
| 81 | 41 | hdpe | 1.0 | 820 | 1.2 |
| 82 | — | PU | — | 800 | ~30 |
| 83 | 19 | PU | 2.0 | 65 | <0.3 |
| 84 | 30 | PU | 1.0 | 55 | <0.3 |
| 85 | 47 | PU | 2.0 | 80 | 0.4 |
| 86 | — | PAN | — | 1000 | 15 |
| 87 | 32 | PAN | 1.0 | 350 | 0.3 |

Table 2-continued (Examples 49 to 93)

Results of the anti-static testing of various thermoplastics

| Example No. | Test substance (Example No.) | Substrate (plastic) | Additive concentration (%) | Charge level (mV) | Half-life period (seconds) |
|---|---|---|---|---|---|
| 88 | — | PA | — | 1200 | >60 |
| 89 | 37 | PA | 2.0 | 900 | 1.5 |
| 90 | 41 | PA | 2.0 | 1000 | 3 |
| 91 | — | PVC (P) | — | 400 | 0.3 |
| 92 | 27 | PVC (P) | 2.0 | 120 | <0.3 |
| 93 | 30 | PVC (P) | 2.0 | 110 | 0.3 |

Table 3

(Examples 94 – 97)

Results of testing the effect of stabilising the processing of polyolefines

| Example No. | Test Substance (Example No.) | Substrate | Additive concentration (%) | Melt indices after extrusions 1 | 3 | 5 |
|---|---|---|---|---|---|---|
| 94 | — | PP | — | | | 38 |
| | | | | 10 | 23 | |
| 95 | 21 | PP | 0.5 | 4.3 | 6.1 | 7.6 |
| 96 | 23 | PP | 0.5 | 4.0 | 7.3 | 8.1 |
| 97 | 45 | PP | 0.5 | 4.3 | 8.1 | 9.1 |

What we claim is:

1. An antistatic mixture of a thermoplastic, comprising (a) a thermoplastic and (b) 0.01 to 5% by weight, relative to the plastic, of one of the substances of formula I or mixtures thereof, said formula being as follows:

$$R-S(-CH_2-CH(R')-O-)_a(CH_2-Y-O-)_nH \quad (I)$$

wherein R' denotes a hydrogen atom and/or the methyl group, Y denotes

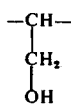

and/or

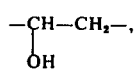

a denotes, as an average value, a number between 1.0 and 12, n denotes, as an average value, a number from 0.5 to 8, R denotes a linear or branched alkyl radical having 8 to 24 carbon atoms, which can preferably be interrupted once by the group —O— or —S—, or denotes phenyl, phenyl substituted by linear or branched alkyl groups, or phenylalkylene having 1 to 3 carbon atoms in the alkylene chain, it being possible for the alkylene chain or the linkage thereof to the phenyl group to be interrupted by a an oxygen or sulphur atom, and for the phenyl radical thereof also to be substituted by linear or branched alkyl groups, and in all cases the whole radical contains 7 to 30 carbon atoms, it being possible, for the case where R' is the methyl group, for R also to denote a linear or branched alkyl group having 1 to 7 carbon atoms, and in all cases of R the sum of the carbon atoms of R and of the radical

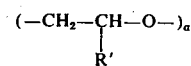

in formula I being 8 to 40.

2. A mixture of plastics according to claim 1, characterised in that n, as an average value, is a number from 1 to 4.

3. A mixture of plastics according to claim 1, characterised in that R denotes an alkyl radical.

4. A mixture of plastics according to claim 1, characterised in that a, as an average value, is a number between 1 and 6 and R' represents a hydrogen atom.

5. A mixture of plastics according to claim 1, characterised in that R represents an alkyl radical having 12 to 18 carbon atoms and R' represents a hydrogen atom.

6. A mixture of plastics according to claim 1, characterised in that R' represents the methyl group or a hydrogen atom.

7. A mixture of plastics according to claim 1, characterised in that the alkylene chain contains 1 carbon atom.

8. A mixture of plastics according to claim 1, characterised in that the phenyl or phenylalkylene radical is substituted by alkyl group which contain 1 to 15 carbon atoms.

9. A mixture of plastics according to claim 8, characterised in that the substituted phenyl or phenylalkylene radical contain 10 to 20 carbon atoms.

10. A mixture of plastics according to claim 1 characterised in that the sum of the carbon atoms of R and of the radical

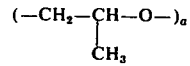

is 10 to 25.

11. A mixture of plastics according to claim 1, characterised in that the plastic is a polyolefine.

12. A mixture of plastics according to claim 11, characterised in that the polyolefine is polypropylene or high pressure polyethylene.

13. A mixture of plastics according to claim 1, characterised in that the thermoplast is polyvinyl chloride.

14. A mixture of plastics according to claim 1, characterised in that the thermoplast is a polyurethane.

15. The composition of claim 1, wherein the formula I is $$CH_3(CH_2)_{11}S(CH_2CH_2O)_2-(CH_2C_2H_3O)_3H.$$
$$\quad\quad\quad\quad\quad\quad\quad\quad\quad\quad\quad\quad\quad |$$
$$\quad\quad\quad\quad\quad\quad\quad\quad\quad\quad\quad\quad\quad OH$$

16. The composition of claim 1, wherein the formula I is $$CH_3(CH_2)_{17}S(CH_2CH_2O)_{1.5}(CH_2C_2H_3O)H$$
$$\quad\quad\quad\quad\quad\quad\quad\quad\quad\quad\quad\quad\quad |$$
$$\quad\quad\quad\quad\quad\quad\quad\quad\quad\quad\quad\quad\quad OH$$

* * * * *